(12) United States Patent
Walsh et al.

(10) Patent No.: US 11,364,030 B2
(45) Date of Patent: Jun. 21, 2022

(54) MEDICAL DEVICE FOR TREATING ESOPHAGEAL ATRESIA

(71) Applicant: BOSTON SCIENTIFIC SCIMED, INC., Maple Grove, MN (US)

(72) Inventors: Michael Walsh, Corofin (IE); Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 167 days.

(21) Appl. No.: 16/791,824

(22) Filed: Feb. 14, 2020

(65) Prior Publication Data

US 2020/0261092 A1 Aug. 20, 2020

Related U.S. Application Data

(60) Provisional application No. 62/806,599, filed on Feb. 15, 2019.

(51) Int. Cl.
*A61B 17/11* (2006.01)
*A61B 17/00* (2006.01)

(52) U.S. Cl.
CPC . *A61B 17/1114* (2013.01); *A61B 2017/00526* (2013.01); *A61B 2017/1132* (2013.01)

(58) Field of Classification Search
CPC ......... A61B 17/1114; A61B 2017/1132; A61B 2017/00893; A61B 2017/1121;
(Continued)

(56) References Cited

U.S. PATENT DOCUMENTS

| 5,527,324 A | 6/1996 | Krantz et al. |
| 5,755,772 A | 5/1998 | Evans et al. |

(Continued)

FOREIGN PATENT DOCUMENTS

| WO | 2009100313 A1 | 8/2009 |
| WO | 2013126246 A1 | 8/2013 |
| WO | 2017202766 A3 | 1/2018 |

OTHER PUBLICATIONS

Damian et al; "Robotic Implant to Apply Tissue Traction Forces in the Treatment of Esophageal Atresia", 2014 IEEE International Convention on Robotics & Automation, 786-792, 2014.
(Continued)

*Primary Examiner* — Jocelin C Tanner
(74) *Attorney, Agent, or Firm* — Seager, Tulle & Wickhem, LLP

(57) ABSTRACT

A medical device for treating esophageal atresia may include a woven tubular member having a first end, a second end, and a body portion extending between the first end and the second end. The first end may have a first flange extending radially outwardly from the body portion. The second end may have a second flange extending radially outwardly from the body portion. The woven tubular member may be configured to transition from an initially-deployed state toward an equilibrium state. In the initially-deployed state, the body portion may include an inner region extending from the first flange to a transition region and an outer region extending from the second flange to the transition region. The outer region may surround the inner region. The woven tubular member may be self-biased to be in the equilibrium state.

19 Claims, 13 Drawing Sheets

(58) Field of Classification Search
CPC .. A61B 2090/3966; A61F 2/07; A61F 2/9661; A61F 2/04; A61F 2/86; A61F 2/88; A61F 2/90; A61F 2002/072; A61F 2002/075
See application file for complete search history.

(56) References Cited

U.S. PATENT DOCUMENTS

| | | | |
|---|---|---|---|
| 6,126,686 A | 10/2000 | Badylak et al. | |
| 6,357,104 B1 | 3/2002 | Myers | |
| 6,626,936 B2 | 10/2003 | Stinson | |
| 7,101,392 B2 | 9/2006 | Heath | |
| 7,282,057 B2 | 10/2007 | Surti et al. | |
| 7,938,852 B2 | 5/2011 | Andreas et al. | |
| 8,579,958 B2 | 11/2013 | Kusleika | |
| 8,621,975 B2* | 1/2014 | Russo | A61F 2/90 87/9 |
| 8,795,301 B2 | 8/2014 | Burnett et al. | |
| 9,168,041 B2 | 10/2015 | Zaritsky et al. | |
| 2008/0114466 A1 | 5/2008 | Shelton | |
| 2009/0012544 A1 | 1/2009 | Thompson et al. | |
| 2009/0192518 A1* | 7/2009 | Golden | A61F 2/966 606/108 |
| 2009/0210048 A1* | 8/2009 | Amplatz | D04C 1/02 623/1.13 |
| 2009/0222076 A1* | 9/2009 | Figulla | A61F 2/2436 623/1.2 |
| 2010/0023046 A1* | 1/2010 | Heidner | A61B 17/12172 606/191 |
| 2010/0286705 A1 | 11/2010 | Vassiliades, Jr. | |
| 2014/0277335 A1 | 9/2014 | Greenberg et al. | |
| 2016/0120638 A1 | 5/2016 | Michalak | |
| 2017/0311952 A1 | 11/2017 | Potter, Jr. et al. | |
| 2018/0228491 A1 | 8/2018 | Potter, Jr. | |

OTHER PUBLICATIONS http://www.we-are-eat.org/innovative-care-managements/growth-induction-foker-procedure-esophageal-atresia/ accessed on Jan. 16, 2020.

https://www.cookmedical.com/newsroom/cook-medicals-flourish-receives-aurhorization-for-pedicatric-esophageal-atresia/ accessed on Jan. 16, 2020.

Oehlerking, et al; "A Hydraulically Controlled Nonoperative Magnetic Treatment for Long Gap Esophageal Atresia", J. Med. Devices 5 (2), 2011.

Tyberg et al; "Endoscopic Ultrasound-Guided Gastrojejunostomy with a Lumen-Apposing Metal Stent: A Mutlicenter, International Experience", Endoscopy International Open 2016; 04: E276-E281, 2016.

Chen et al.; "EUS-Guided Gastroenterostomy is Comparable to Enteral Stenting with Fewer Re-Interventions in Malignant Gastic Outlet Obstruction," Surg Endosc. 31(7): 2946-2952, 2017.

Ge et al; "EUS Guided Gastrojejunostomy with Lumen Apposing Metal Stent Placement for Palliation of Malignant Gastric Outlet Obstruction", Gastrointestinal Endoscopy vol. 87, No. 6S, 2018.

* cited by examiner

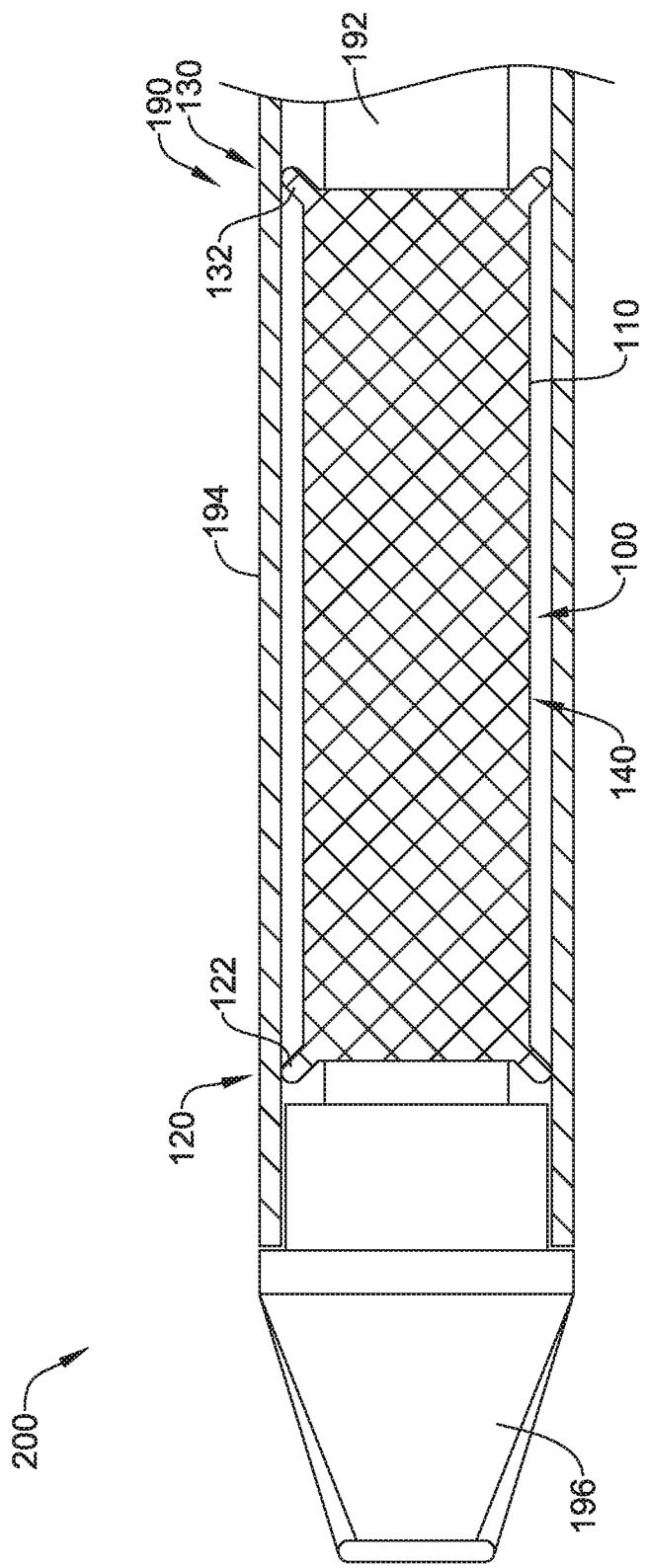

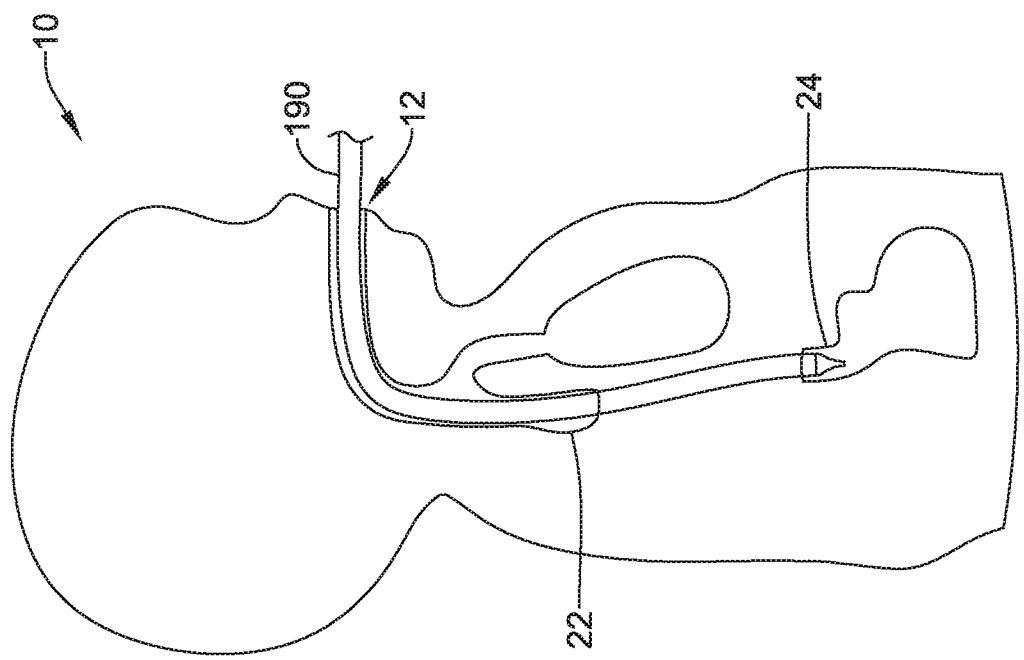

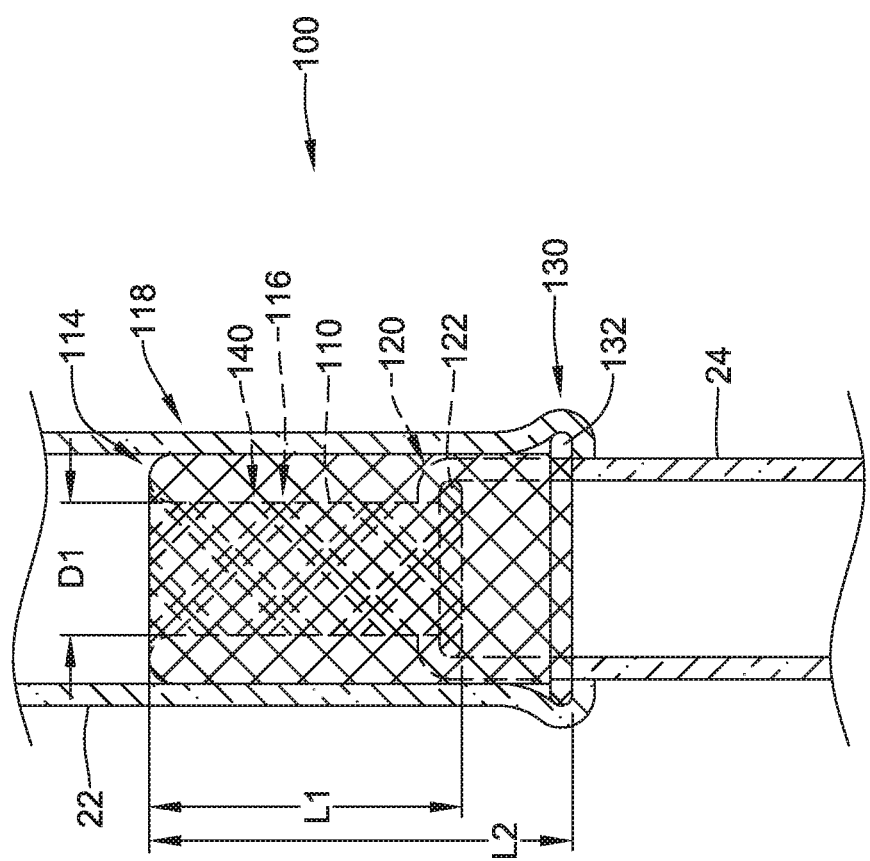

MEDICAL DEVICE FOR TREATING ESOPHAGEAL ATRESIA

CROSS-REFERENCE TO RELATED APPLICATIONS

This application claims the benefit of priority under 35 U.S.C. § 119 of U.S. Provisional Application No. 62/806,599 filed Feb. 15, 2019, the entire disclosure of which is hereby incorporated by reference.

TECHNICAL FIELD

The present disclosure pertains to medical devices, and methods for using medical devices. More particularly, the present disclosure pertains to medical devices for treating esophageal atresia.

BACKGROUND

Esophageal atresia is a condition where individuals are born with an incomplete esophagus which does not connect the throat to the stomach. There are several different types of esophageal atresia situations which makes it difficult for the current corrective procedures to be performed successfully. Moreover, the current procedures, for example the Foker Technique, are very invasive and may cause extreme trauma. In some cases, individuals are paralyzed and made unconscious (sedated) for several weeks which may cause weight loss and muscle wasting. The Foker Technique uses sutures which are attached to both pouch ends of the esophagus. The sutures are periodically pulled a small amount, allowing the esophagus to grow around 5 cm each time and stretch the esophagus over time. During that time, the individuals remain paralyzed and unconscious. Another shortcoming of this procedure is that the applied forces are uncontrolled and can leave the blood at the end of the esophagus unable to perfuse. In another alternative, magnets are implanted into each of the pouch ends of the esophagus and their attraction to each other stretches the pouch ends of the esophagus towards each other over time. However, long-term sedation and/or immobilization, mucous and/or saliva aspiration, and alternative feeding procedures are still required, as is a surgical procedure to later remove the magnets and connect the pouch ends. As such, there is an ongoing need to provide alternative medical devices and procedures for treating esophageal atresia.

SUMMARY

In a first aspect, a medical device for treating esophageal atresia may comprise a woven tubular member having a first end, a second end, and a body portion extending between the first end and the second end. The first end may have a first flange extending radially outwardly from the body portion. The second end may have a second flange extending radially outwardly from the body portion. The woven tubular member may be configured to transition from an initially-deployed state toward an equilibrium state. In the initially-deployed state, the body portion may include an inner region extending from the first flange to a transition region and an outer region extending from the second flange to the transition region. The outer region may surround the inner region. The woven tubular member may be self-biased to be in the equilibrium state.

In addition or alternatively, an axial length of the inner region decreases and an axial length of the outer region increases as the woven tubular member transitions from the initially-deployed state toward the equilibrium state.

In addition or alternatively, in the equilibrium state, the first flange is disposed within the outer region.

In addition or alternatively, the medical device may further comprise a covering disposed on at least a portion of the woven tubular member.

In addition or alternatively, at least one of the first flange and the second flange includes the covering.

In addition or alternatively, the covering at least partially encapsulates the woven tubular member.

In addition or alternatively, an outer diameter of the inner region increases as its axial length decreases.

In addition or alternatively, a portion of the body portion is everted from the inner region to the outer region as the woven tubular member transitions from the initially-deployed state toward the equilibrium state.

In addition or alternatively, a method of manufacturing a medical device for treating esophageal atresia may comprise: forming a woven tubular member having a first end, a second end, and a body portion extending between the first end and the second end, the woven tubular member including: a first flange extending radially outwardly from the body portion at the first end, and a second flange extending radially outwardly from the body portion at the second end; disposing a tubular spacer around the body portion; everting the second end back over the tubular spacer to define an inner region of the body portion within the tubular spacer and an outer region of the body portion surrounding the tubular spacer; and annealing the woven tubular member to define an equilibrium state in which the outer region surrounds the inner region.

In addition or alternatively, the method may further comprise removing the tubular spacer after annealing the woven tubular member.

In addition or alternatively, the method may further comprise disposing a covering on the body portion between the first end and the second end.

In addition or alternatively, the covering extends over the first flange and the second flange.

In addition or alternatively, the outer region surrounds the first flange in the equilibrium state.

In addition or alternatively, the woven tubular member is self-biased to be in the equilibrium state after annealing the woven tubular member.

In addition or alternatively, the method may further comprise partially annealing the woven tubular member after disposing the tubular spacer around the body portion but before everting the second end back over the tubular spacer.

In addition or alternatively, a medical device for treating esophageal atresia may comprise a woven tubular member having a first end, a second end, and a body portion extending between the first end and the second end. The first end may have a first flange extending radially outwardly from the body portion. The second end may have a second flange extending radially outwardly from the body portion. The body portion may have an inner region extending from the first flange to a transition region and an outer region extending from the second flange to the transition region. The outer region may surround the inner region. The woven tubular member may be configured to transition from an initially-deployed state toward an equilibrium state. A portion of the body portion may be everted from the inner region to the outer region as the woven tubular member transitions from the initially-deployed state toward the equilibrium state.

In addition or alternatively, the first flange moves toward the second flange as the woven tubular member transitions from the initially-deployed state toward the equilibrium state.

In addition or alternatively, the outer region of the woven tubular member surrounds the first flange in the equilibrium state.

In addition or alternatively, an outer diameter of the inner region increases as the woven tubular member transitions from the initially-deployed state toward the equilibrium state.

In addition or alternatively, in the initially-deployed state, the woven tubular member has a proximalmost extent and a distalmost extent, the second flange being positioned at a location intermediate the proximalmost extent and the distalmost extent.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 7A illustrates alternative aspects of a system for treating esophageal atresia; and FIGS. 8-12 illustrate the use of a system and/or medical device for treating esophageal atresia.

Figure 1:
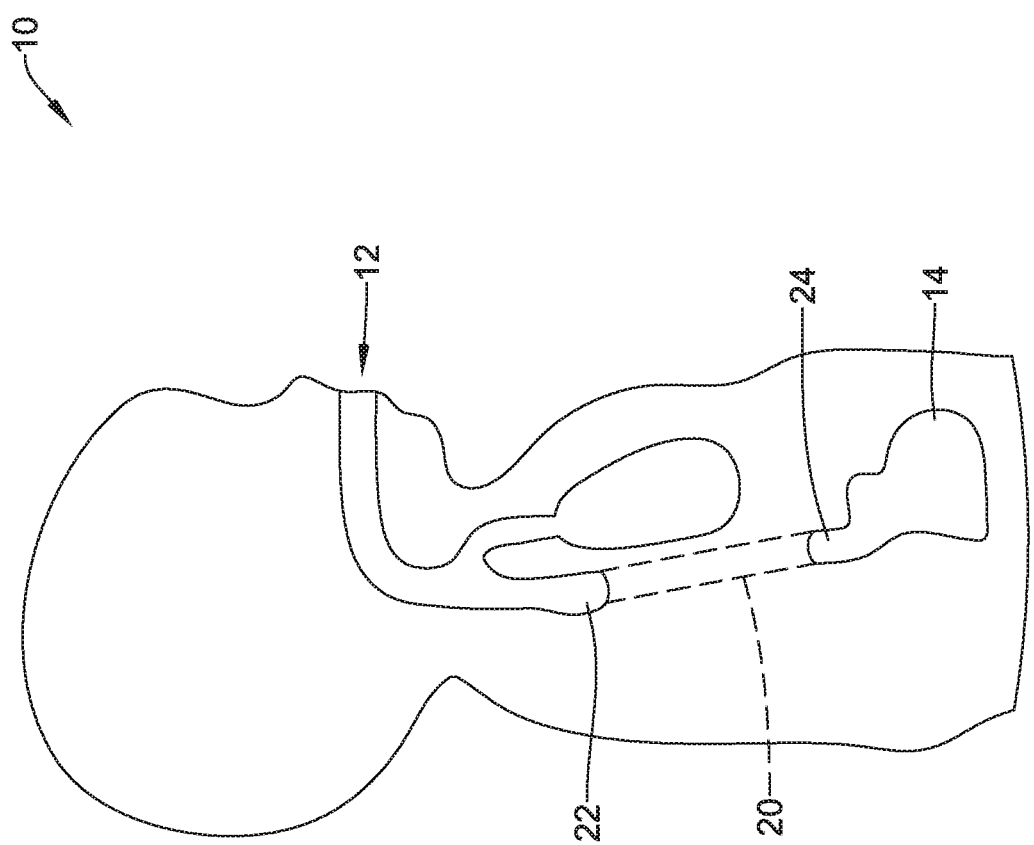
FIG. 1 schematically illustrates aspects of esophageal atresia.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified. As such, in any given figure, some features may not be shown, or may be shown schematically, for simplicity. Additional details regarding some components, configurations, and/or embodiments may be illustrated in other figures in greater detail.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together. A monolithic and/or unitary element shall generally be inseparable without physically destroying the element and/or device of which it is a part.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, that feature, structure, or characteristic may be used in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates aspects of an example of esophageal atresia, which is a congenital defect affecting a number of babies each year. As shown in FIG. 1, a patient 10 may be born with an esophagus 20 that is incomplete, resulting in the patient 10 having an upper esophagus pouch 22 connected to the mouth 12 and a lower esophagus pouch 24 connected to the stomach 14. The upper esophagus pouch 22 and the lower esophagus pouch 24 may be spaced apart from each other within the torso of the patient 10, such that the upper esophagus pouch 22 is unconnected or discontinuous with the lower esophagus pouch 24. This disclosure describes medical devices and/or systems for treating pediatric esophageal atresia without subjecting the patient 10 to (or with reduced) long-term sedation and/or immobilization, mucous and/or saliva aspiration, and/or alternative feeding procedures.

Figure 2:
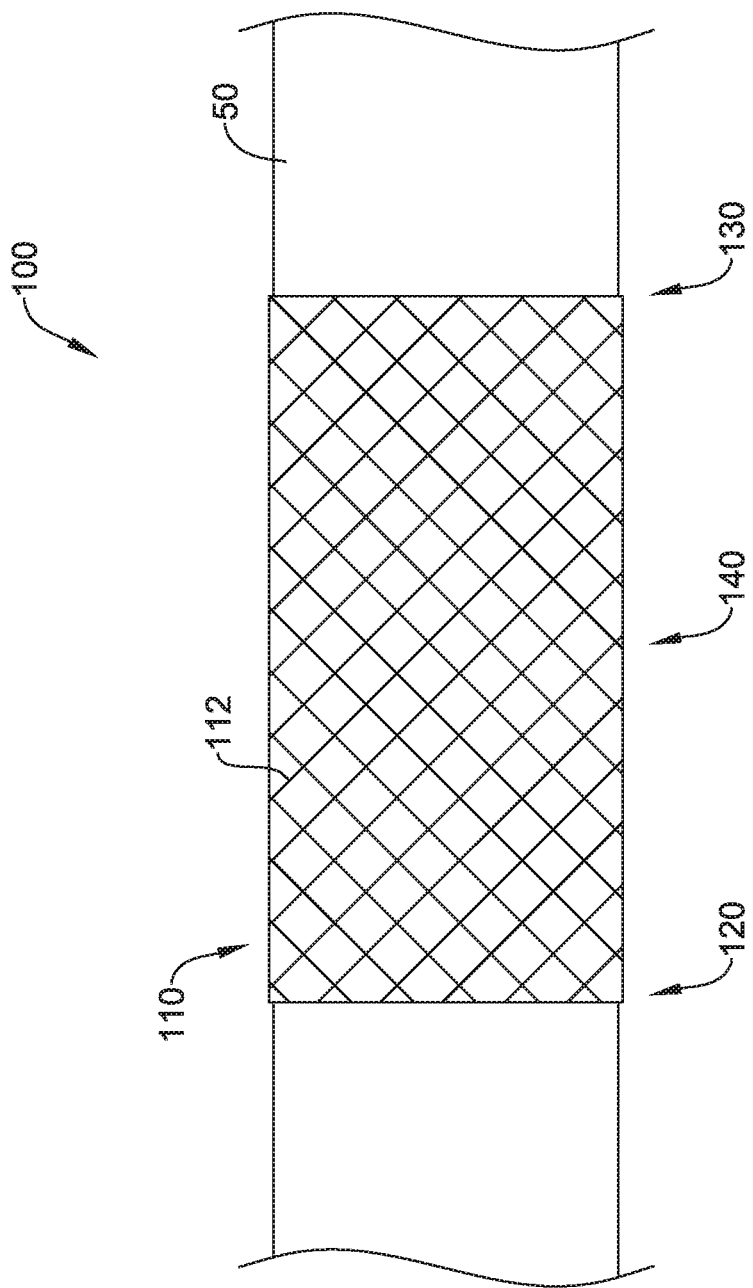
FIGS. 2-6 illustrate an example method of manufacturing a medical device for treating esophageal atresia.

FIGS. 2-6 illustrate a method of manufacturing a medical device 100 for treating esophageal atresia. An example of the resulting and/or completed medical device 100 may be seen in FIG. 6, for reference. The method may include forming a woven tubular member 110. In some embodiments, and as shown in FIG. 2, the woven tubular member 110 may be formed on a mandrel 50 or the woven tubular member 110 may be disposed on the mandrel 50 after forming the woven tubular member 110. In some embodiments, the mandrel 50 may be omitted from the method of manufacturing. The woven tubular member 110 may have a first end 120, a second end 130, and a body portion 140 extending between the first end 120 and the second end 130. The woven tubular member 110 may be self-expanding, although other means of expansion (e.g., balloon expansion, mechanical expansion, etc.) may also be used. The woven tubular member 110 may include and/or define a lumen extending longitudinally from the first end 120 to the second end 130, and/or through the body portion 140. The first end 120 and the second end 130 may be axially and/or longitudinally open into the lumen. The woven tubular member 110, the body portion 140, and/or the lumen may define and/or be coaxial with a central longitudinal axis.

The woven tubular member 110 may be formed from one or more, or a plurality of filaments 112 interwoven in an alternating and/or repeating over-and-under relationship. The one or more filaments 112 may comprise one individual filament, two individual filaments, three individual filaments, four individual filaments, or another suitable number of individual filaments (e.g., five, eight, ten, twelve, sixteen, thirty-two etc.). In some embodiments, the one or more filaments 112 may be a single continuous filament interwoven with itself. In some embodiments, the one or more filaments 112 may be a plurality of filaments interwoven (around the mandrel 50, for example) sequentially, simultaneously, and/or a combination thereof. In some embodiments, the one or more filaments 112 may extend along a longitudinal length of the woven tubular member 110. In some embodiments, the one or more filaments 112 may be arranged helically, spirally, angled circumferentially, or another suitable arrangement. In some embodiments, the one or more filaments 112 may form a plurality of crossing points when interwoven together and/or formed into the woven tubular member 110, wherein each of the plurality of crossing points is formed by an upper filament portion of the one or more filaments 112 (e.g., a radially outwardly positioned filament portion) crossing over a lower filament portion of the one or more filaments 112 (e.g., a radially inwardly positioned filament portion). In at least some embodiments, the one or more filaments 112 may preferably be braided to form the woven tubular member 110 or a braided tubular member or stent, such as by an example braiding machine (not shown). In some embodiments, the woven tubular member 110 may be formed by other means, including but not limited to, weaving, knitting, etc.

In some embodiments, the woven tubular member 110 may include one plurality of crossing points, or the woven tubular member 110 may include more than one plurality of crossing points and/or additional pluralities of crossing points. In some embodiments, all of the pluralities of crossing points may include similar characteristics, structure, and/or features, or some of the pluralities of crossing points may include differing characteristics, structure, and/or features. In some embodiments, the one or more filaments 112 at the first end 120 may be substantially similar to and/or a mirror image of the one or more filaments 112 at the second end 130. In some embodiments, the one or more filaments 112 at the first end 120 may be arranged differently than at the second end 130. Some suitable, but non-limiting, examples of materials, including but not limited to shape memory materials, for the woven tubular member 110 and/or the one or more filaments 112 are discussed below.

Figure 3:
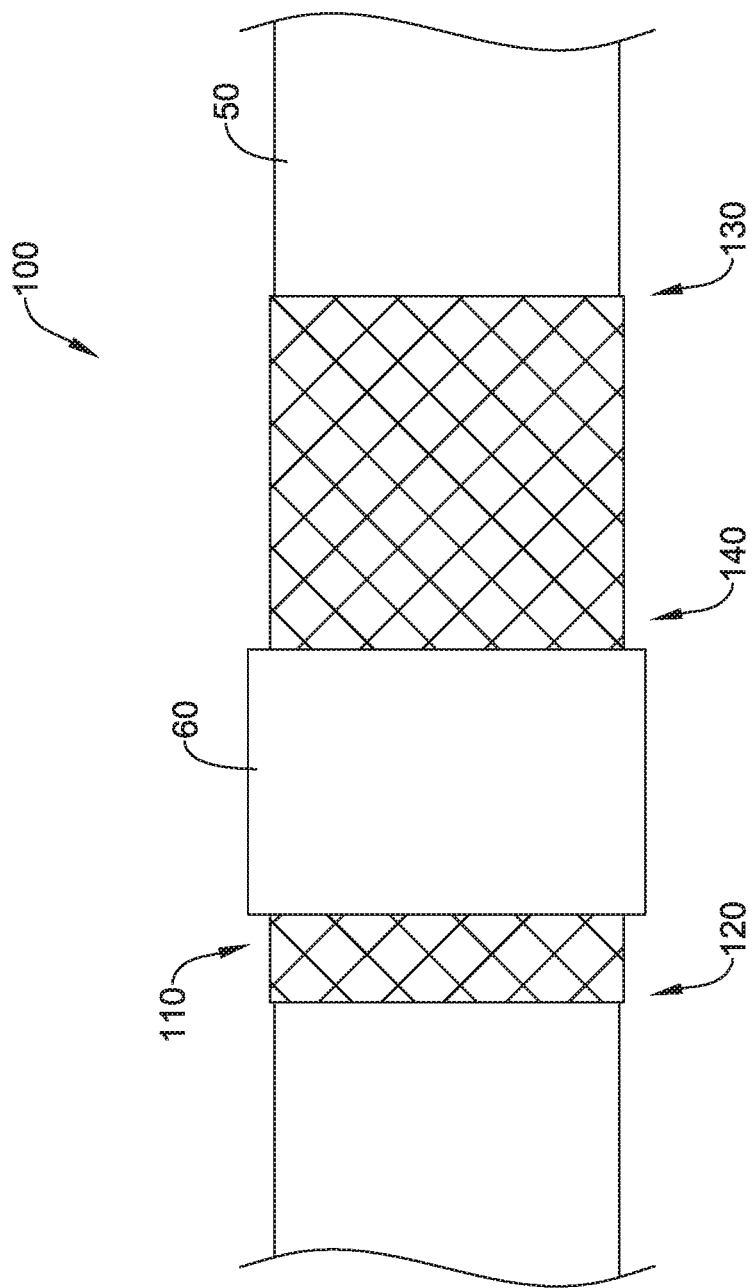

The method of manufacturing the medical device 100 may include disposing a tubular spacer 60 over the body portion 140 of the woven tubular member 110 and the mandrel 50 (if present), as shown in FIG. 3, such that the tubular spacer 60 surrounds the body portion 140 of the woven tubular member 110. In some embodiments, the tubular spacer 60 may be annular. In some embodiments, the tubular spacer 60 may include cutouts and/or recesses formed therein. In some embodiments, the tubular spacer 60 may have a wall thickness defined by an outer surface and an inner surface spaced radially inward of the outer surface. In some embodiments, the tubular spacer 60 may be positioned proximate and/or closer to the first end 120 of the woven tubular member 110 than the second end 130 of the woven tubular member 110, proximate and/or closer to the second end 130 of the woven tubular member 110 than the first end 120 of the woven tubular member 110, or substantially centered along the body portion 140 of the woven tubular member 110, depending upon a desired equilibrium configuration (as discussed herein) of the medical device 100 when finished. Some suitable, but non-limiting, examples of materials for the tubular spacer 60 are discussed below.

Figure 4:
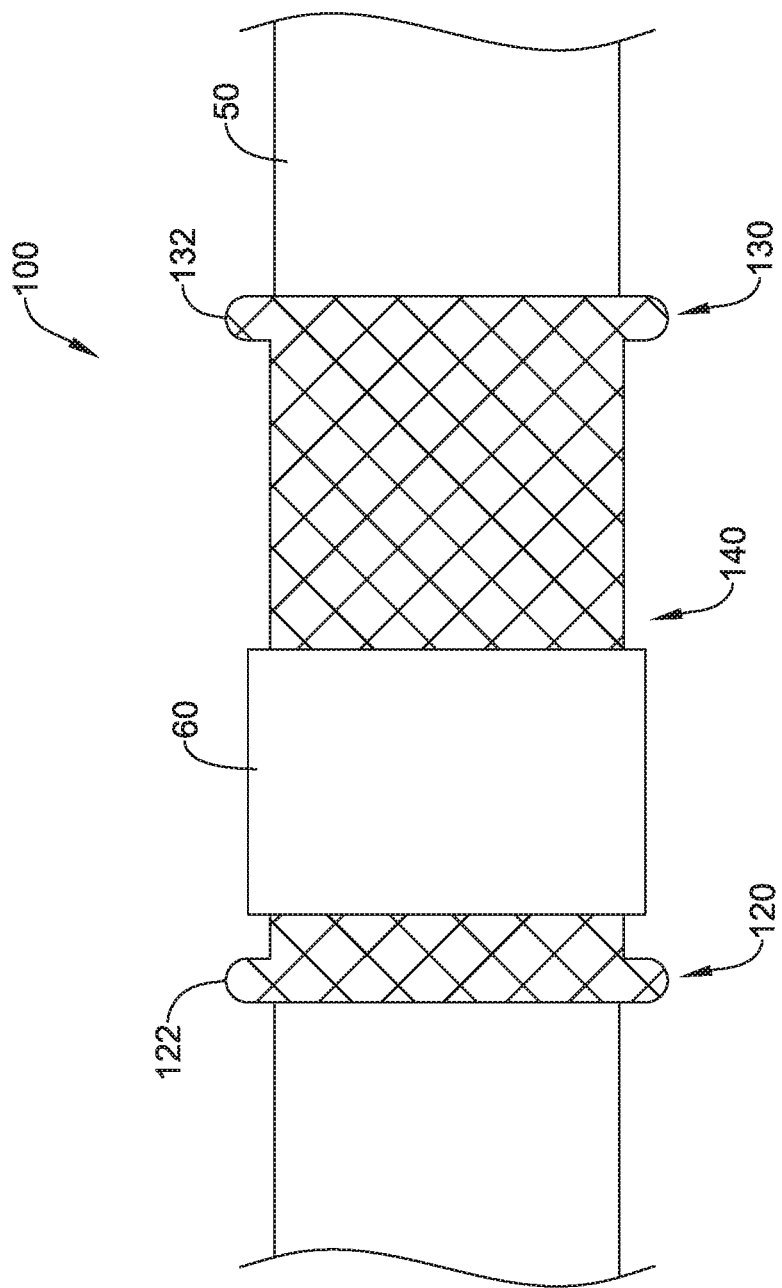

The method of manufacturing the medical device 100 may include forming a first flange 122 extending radially outward from the body portion 140 at the first end 120. The method of manufacturing the medical device 100 may include forming a second flange 132 extending radially outward from the body portion 140 at the second end 130. FIG. 4 illustrates the woven tubular member 110 with the first flange 122 formed at the first end 120, the second flange 132 formed at the second end 130, and the tubular spacer 60 disposed over the body portion 140. The exact order or sequence of forming the first flange 122, forming the second flange 132, and disposing the tubular spacer 60 over the body portion 140 may be varied and/or altered without substantially affecting or hindering the method of manufacturing the medical device 100. For example, if the first flange 122 and the second flange 132 are formed prior to disposing the tubular spacer 60 over the body portion 140, one of the first flange 122 and the second flange 132 may be compressed or deflected to permit the tubular spacer 60 to be slid over the respective flange and onto the body portion 140. In another example, the tubular spacer 60 may be disposed over the body portion 140 prior to forming one or both of the first flange 122 and the second flange 132.

Figure 5:
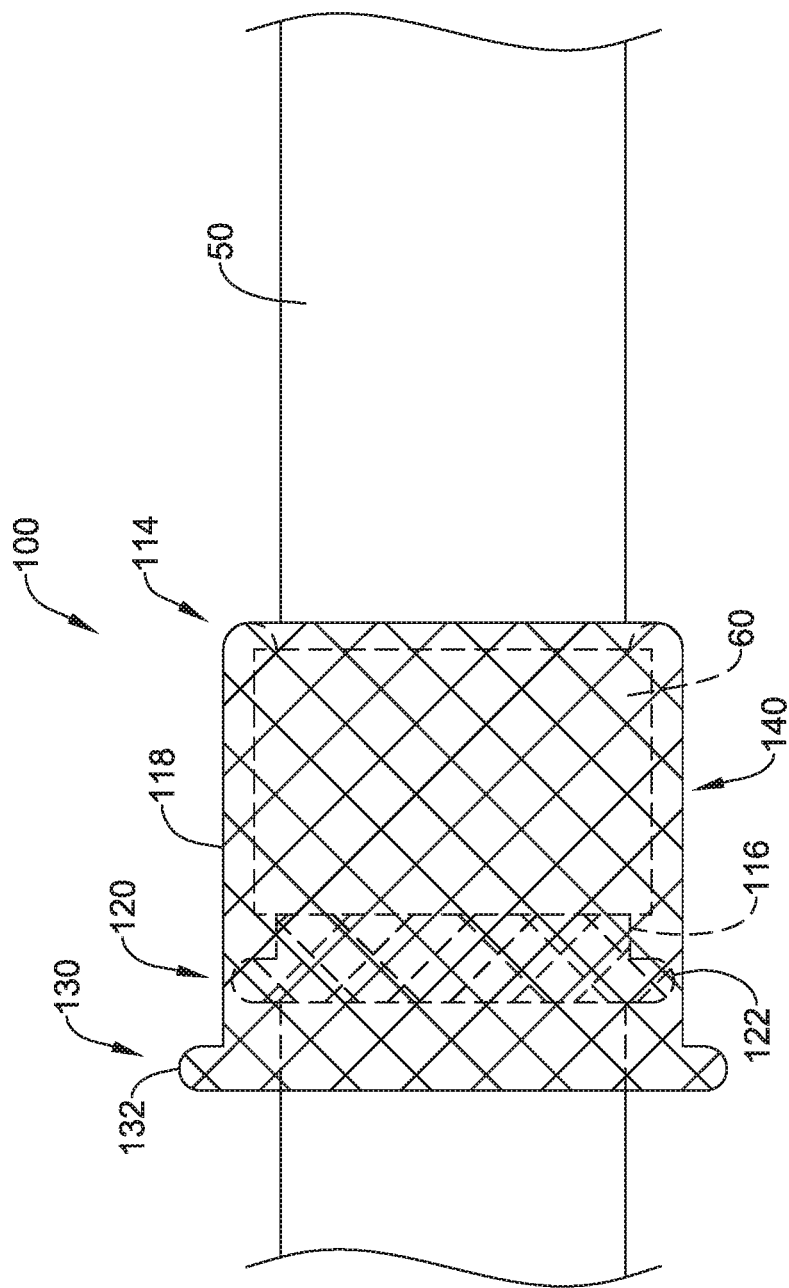

In some embodiments, the method of manufacturing the medical device 100 may include everting the second end 130 back over and/or around the body portion 140 and the tubular spacer 60 at a transition region 114 to define an inner region 116 of the body portion 140 within the tubular spacer 60 and an outer region 118 of the body portion 140 surrounding the tubular spacer 60 and/or the inner region 116, as shown in FIG. 5. The inner region 116 may extend from the first flange 122 to the transition region 114. The outer region 118 may extend from the second flange 132 to the transition region 114. The inner region 116 may be disposed radially inward of the outer region 118 and/or the outer region 118 may be disposed radially outward of the inner region 116.

The method of manufacturing the medical device 100 may include annealing (e.g., heat-setting) the woven tubular member 110 after everting the second end 130 back over the body portion 140 and the tubular spacer 60 to define an equilibrium state of the woven tubular member 110 in which the outer region 118 circumferentially surrounds the inner region 116 and/or the body portion 140. The equilibrium state of the woven tubular member 110 may be seen in FIGS. 5 and 6 for example. The woven tubular member 110 may be self-biased to be in the equilibrium state after annealing (e.g., heat-setting) the woven tubular member 110. In some embodiments, everting the second end 130 back over and/or around the body portion 140 and the tubular spacer 60 may further define a desired ending length of the woven tubular member 110 in the equilibrium state that is less than a length of the woven tubular member 110 in an initially-deployed state, as will be described further herein. In at least some embodiments, in the equilibrium state, the first end 120 and/or the first flange 122 of the woven tubular member 110 is disposed within the outer region 118 and/or the body portion 140 of the woven tubular member 110. In other words, in some embodiments, the first end 120 and/or the first flange 122 of the woven tubular member 110 may be positioned between the second end 130 and/or the second flange 132 and the transition region 114 in the equilibrium state.

In some embodiments, the method of manufacturing the medical device 100 may further comprise partially annealing the woven tubular member 110 after disposing the tubular spacer 60 over the body portion 140 but before everting the second end 130 back over and/or around the body portion 140 and the tubular spacer 60. Partially annealing the woven tubular member 110 after forming the first flange 122 and the second flange 132 and/or before everting the second end 130 back over and/or around the body portion 140 and the tubular spacer 60 may maintain shape and memory function of the woven tubular member 110, and/or may set a shape of the first flange 122 and the second flange 132 relative to the body portion 140. For example, in some embodiments, one and/or both of the first flange 122 and the second flange 132 may extend substantially perpendicular to the body portion 140, the lumen, and/or the central longitudinal axis of the woven tubular member 110. In some embodiments, the first flange 122 and/or the second flange 132 may extend radially outward from an outer surface of the body portion 140 of the woven tubular member 110 at least as far as a radial thickness of the tubular spacer 60.

Figure 6:
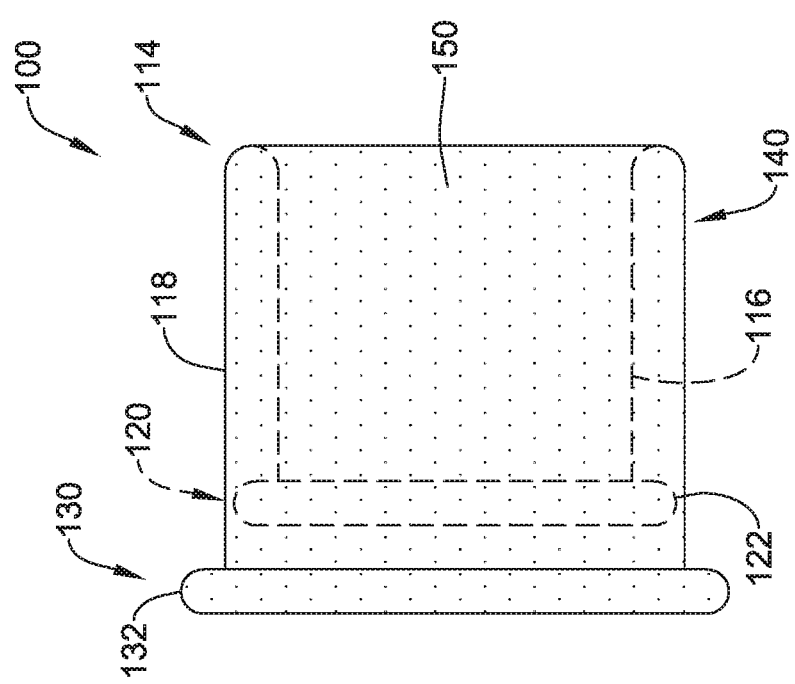

The method of manufacturing the medical device 100 may further comprise removing the tubular spacer 60 after annealing the woven tubular member 110. Additionally, the method of manufacturing the medical device 100 may further comprise forming, applying, and/or disposing a covering 150 on at least a portion of the woven tubular member 110. For example, the covering may be disposed on the body portion 140 between the first end 120 of the woven tubular member 110 and the second end 130 of the woven tubular member 110, as shown in FIG. 6. In some embodiments, the first flange 122 and/or the second flange 132 may be devoid of the covering 150. In at least some embodiments, the covering 150 extends over one or both of the first flange 122 and the second flange 132. In some embodiments, at least one of the first flange 122 and the second flange 132 includes the covering 150. In some embodiments, the covering 150 is disposed at least partially within the inner region 116 and at least partially outside of the outer region 118 in the equilibrium state. In some embodiments, the covering 150 may be impermeable to fluids and/or gases. In some embodiments, the covering 150 may be a separate structure (e.g. a sleeve, a membrane, a tubular body, etc.) attached to, coupled to, and/or disposed on or about at least a portion of the woven tubular member 110. In some embodiments, the covering 150 may be a coating applied to the woven tubular member 110. In some embodiments, the covering 150 at least partially encapsulates the woven tubular member 110. In some embodiments, the covering 150 completely encapsulates the woven tubular member 110. Some suitable, but non-limiting, examples of materials for the covering 150 are discussed below.

Figure 7:
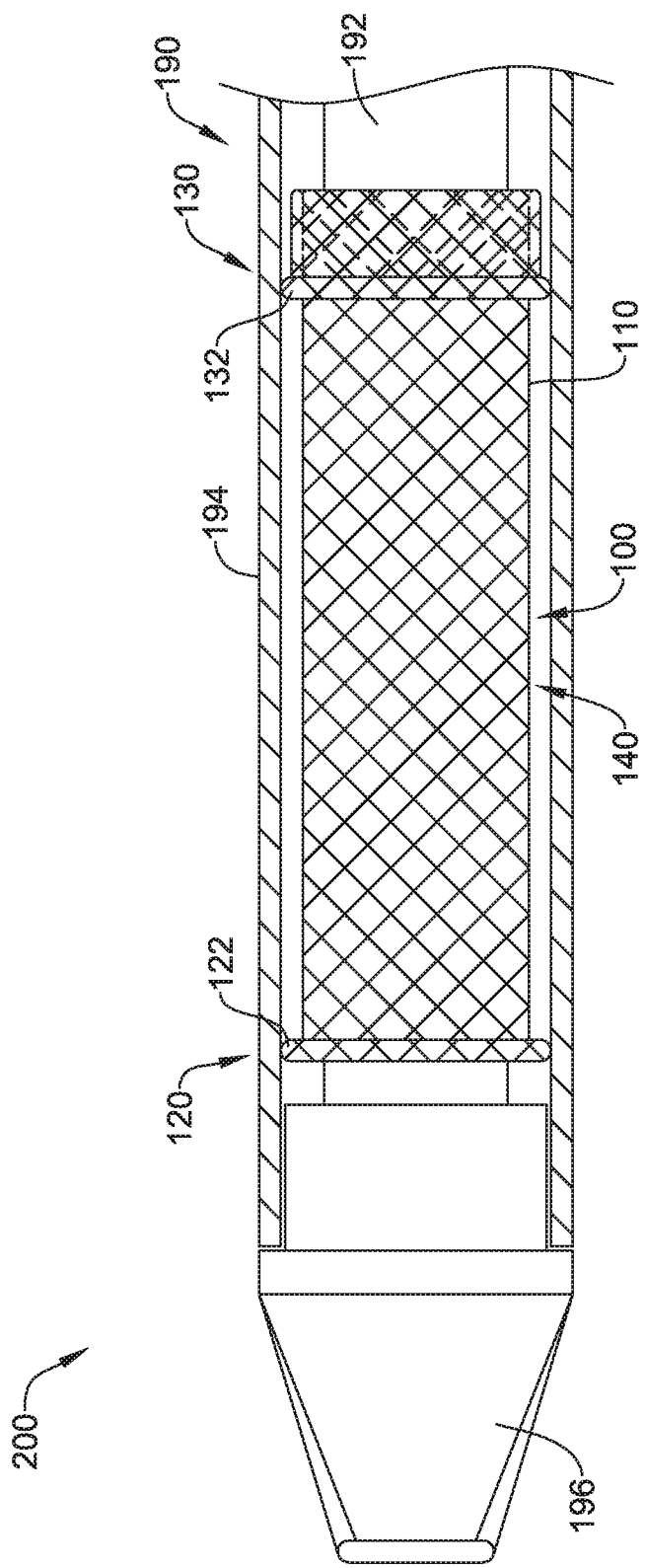
FIG. 7 illustrates aspects of a system for treating esophageal atresia.

FIGS. 7 and 7A are partial cross-sectional views illustrating aspects of a system 200 for treating esophageal atresia. The system 200 may include a delivery device 190 having an inner tubular member 192 and an outer tubular member 194 disposed about and longitudinally slidable relative to the inner tubular member 192. In some embodiments, the delivery device 190 may include a proximal handle. The delivery device 190 may include a distal tip 196 attached and/or fixed to the inner tubular member 192. In some embodiments, the distal tip 196 may be a cautery tip configured to cut and cauterize tissue in separate and/or simultaneous steps or procedures. In some embodiments, the system 200 and/or the delivery device 190 may be operably connected to a source of energy for driving the cautery tip. The system 200 may include the medical device 100 disposed between the inner tubular member 192 and the outer tubular member 194, with the woven tubular member 110 constrained in a delivery state.

In some embodiments, in the delivery state, the first flange 122 and/or the second flange 132 may be oriented generally perpendicular to a central longitudinal axis of the delivery device 190, the medical device 100, and/or the woven tubular member 110, as shown in FIG. 7. In at least some embodiments, the second end 130 of the woven tubular member 110 may be positioned, arranged, and/or configured with the second flange 132 everted and/or disposed about the body portion 140 in the delivery state. In some embodiments, in the delivery state, the first flange 122 and/or the second flange 132 may be oriented at an oblique angle relative to the central longitudinal axis of the delivery device 190, the medical device 100, and/or the woven tubular member 110, as shown in FIG. 7A. In some embodiments, the first flange 122 and/or the second flange 132 may extend axially or longitudinally away from the body portion 140 at the oblique angle. In some embodiments, the first flange 122 and/or the second flange 132 may be self-biased to be oriented generally perpendicular to the central longitudinal axis of the delivery device 190, the medical device 100, and/or the woven tubular member 110 upon deployment.

Other configurations of the first flange 122 and/or the second flange 132 in the delivery state are also contemplated, including but not limited to, extending axially or longitudinally from and/or alongside the body portion 140 generally parallel with the central longitudinal axis of the delivery device 190, the medical device 100, and/or the woven tubular member 110. Some suitable, but non-limiting, examples of materials for the delivery device 190, the inner tubular member 192, the outer tubular member 194, and/or the distal top 196, including but not limited to polymeric and/or metallic materials, are discussed below.

FIGS. 8-12 illustrate the placement and use of the medical device 100 in a patient 10 with esophageal atresia. For clarity, the covering 150 has been omitted from the medical device 100 shown in FIGS. 9-12. In the interest of brevity, FIGS. 8-12 illustrate an example of an oral approach to placement and use of the medical device 100, and the disclosure is presented with respect thereto. However, other approaches, including but not limited to a gastric approach, are also contemplated within the scope of the disclosure. As shown in FIG. 8, the delivery device 190 may be inserted into the mouth 12 of the patient 10. The delivery device 190 may be advanced into and through the upper esophagus pouch 22. An opening may be formed in the upper esophagus pouch 22 to permit passage of the delivery device 190. For example, the cautery tip may be used to cut and cauterize the opening in the upper esophagus pouch 22. Other means and/or methods of forming the opening are also contemplated. The delivery device 190 may be advanced through the torso of the patient 10 to a position adjacent the lower esophagus pouch 24. In some embodiments, the delivery device 190 may be configured to permit, facilitate, and/or provide visualization across the gap between the upper esophagus pouch 22 and the lower esophagus pouch 24. An opening may be formed in the lower esophagus pouch 24 to permit passage of the delivery device 190. For example, the cautery tip may be used to cut and cauterize the opening in the lower esophagus pouch 24. Other means and/or methods of forming the opening are also contemplated. For example, one or both of the opening in the upper esophagus pouch 22 and the opening in the lower esophagus pouch 24 may be formed by surgical means and/or a cutting device. Use of a cautery tip on the delivery device 190 may permit fewer devices and/or tools to be used during the procedure, thereby speeding up the procedure and/or subjecting the patient to less trauma. The medical device 100 may be deployed by retracting and/or slidably translating the outer tubular member 194 proximally relative to the inner tubular member 192, thereby releasing the medical device 100 and permitting the woven tubular member 110 to radially expand and/or transition into an initially-deployed state by everting the second end 130 and/or the second flange 132 back over the body portion 140 toward the first end 120 and/or the first flange 122.

Figure 9:
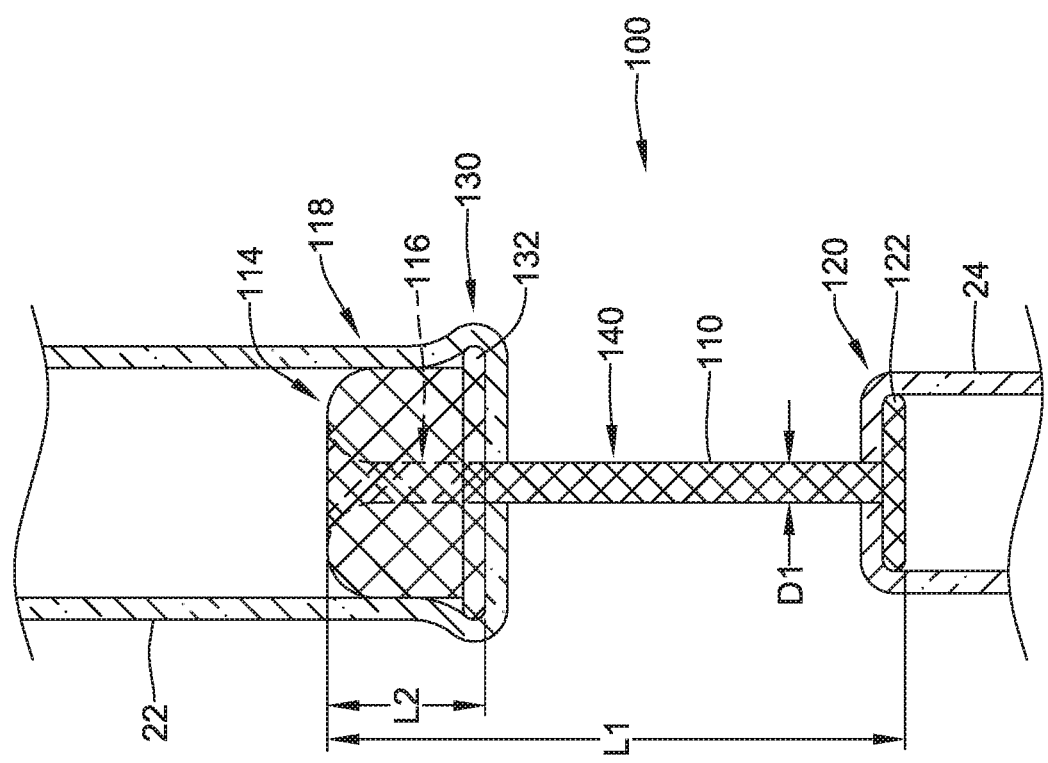

FIG. 9 illustrates the medical device 100 and/or the woven tubular member 110 in the initially-deployed state in which the woven tubular member 110 is deformed away from its equilibrium state (e.g., longitudinally stretched) by placing the woven tubular member 110 in tension. The first end 120 of the woven tubular member 110 may be disposed within the lower esophagus pouch 24. The first flange 122 may extend radially outward from the body portion 140 of the woven tubular member 110 within the lower esophagus pouch 24. The first flange 122 may have an outer diameter greater than a diameter of the opening formed in the lower esophagus pouch 24. The first flange 122 may anchor the woven tubular member 110 within the lower esophagus pouch 24. The first flange 122 may be configured to prevent the first end 120 from pulling and/or translating through the opening formed in the lower esophagus pouch 24. In some embodiments, the first flange 122 may extend generally or substantially perpendicular to the body portion 140 and/or the central longitudinal axis. In some embodiments, the first flange 122 may include a surface facing away from the first end 120 (e.g., towards the second end 130 in the initially-deployed state) that is oriented perpendicular to the body portion 140 and/or the central longitudinal axis. In some embodiments, the first flange 122 may be fixedly secured to the lower esophagus pouch 24. For example, the first flange 122 may be sutured and/or bonded (e.g., adhered) to the lower esophagus pouch 24. In some embodiments, the first flange 122 may be configured to permit and/or promote tissue ingrowth into the first flange 122. In some embodiments, the first flange 122 may include the covering 150, thereby preventing tissue ingrowth into the first flange 122.

The second end 130 of the woven tubular member 110 may be disposed within the upper esophagus pouch 22. The second flange 132 may extend radially outward from the body portion 140 of the woven tubular member 110 within the upper esophagus pouch 22. The second flange 132 may have an outer diameter greater than a diameter of the opening formed in the upper esophagus pouch 22. The second flange 132 may anchor the woven tubular member 110 within the upper esophagus pouch 22. The second flange 132 may be configured to prevent the second end 130 from pulling and/or translating through the opening formed in the upper esophagus pouch 22. In some embodiments, the second flange 132 may extend generally or substantially perpendicular to the body portion 140 and/or the central longitudinal axis. In some embodiments, the second flange 132 may include a surface facing away from the second end 130 (e.g., towards the first end 120 in the initially-deployed state) that is oriented perpendicular to the body portion 140 and/or the central longitudinal axis. In some embodiments, the second flange 132 may be fixedly secured to the upper esophagus pouch 22. For example, the second flange 132 may be sutured and/or bonded (e.g., adhered) to the upper esophagus pouch 22. In some embodiments, the second flange 132 may be configured to permit and/or promote tissue ingrowth into the second flange 132. In some embodiments, the second flange 132 may include the covering 150, thereby preventing tissue ingrowth into the second flange 132.

In the initially-deployed state, the body portion 140 may include an inner region 116 extending from the first flange 122 to a transition region 114 and an outer region 118 extending from the second flange 132 to the transition region 114. The transition region 114 may be defined and/or considered as a part of the body portion 140 where eversion occurs (e.g., where the inner region 116 everts and/or transitions to the outer region 118). In the initially-deployed state, the inner region 116 and the outer region 118 may extend from the transition region 114 in a common axial direction. For example, the inner region 116 may extend from the transition region 114 in a first axial direction along the central longitudinal axis, and the outer region 118 may extend from the transition region 114 in the first axial direction along the central longitudinal axis. In the initially-deployed state, the outer region 118 may surround the inner region 116. In the initially-deployed state, the woven tubular member 110 has a proximalmost extent and a distalmost extent. In the initially-deployed state, the second flange 132 may be positioned at a location intermediate the proximalmost extent and the distalmost extent. For example, the second flange 132 may be disposed at an axial or longitudinal position located between the proximalmost extent and the distalmost extent of the woven tubular member 110. The inner region 116 may have and/or define an outer diameter D1. In the initially-deployed state, the outer diameter D1 of the inner region 116 may be reduced and/or smaller compared to the outer diameter D1 of the inner region 116 in the equilibrium state.

Figure 10:
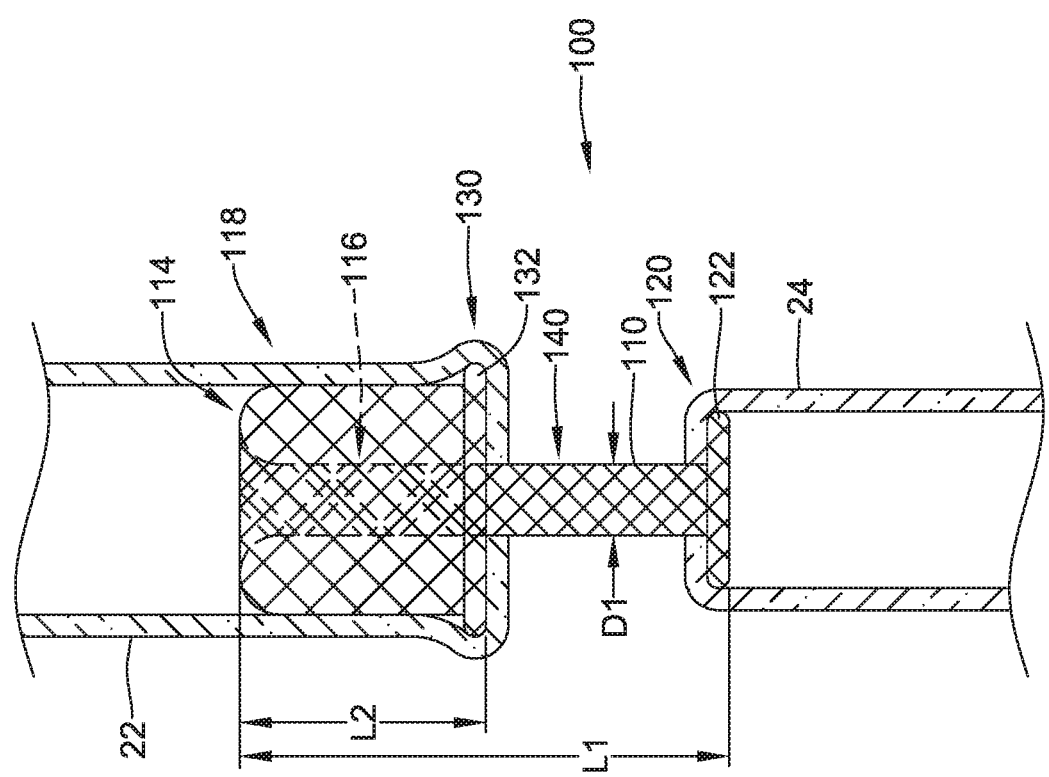

The woven tubular member 110 may be configured to transition from the initially-deployed state toward the equilibrium state. FIG. 10 illustrates the medical device 100 and/or the woven tubular member 110 in a partially-transitioned state between the initially-deployed state and the equilibrium state. As may be seen from FIG. 10, an axial length L1 of the inner region 116 of the body portion 140 decreases and an axial length L2 of the outer region 118 of the body portion 140 increases as the woven tubular member 110 transitions from the initially-deployed state toward the equilibrium state. In at least some embodiments, the outer diameter D1 of the inner region 116 of the body portion 140 increases as the axial length L1 of the inner region 116 of the body portion 140 decreases and/or as the woven tubular member 110 transitions from the initially-deployed state toward the equilibrium state. As may be seen in the figures, a portion of the body portion 140 is everted from the inner region 116 to the outer region 118 as the woven tubular member 110 transitions from the initially-deployed state toward the equilibrium state.

As noted herein, the woven tubular member 110 is self-biased to be in the equilibrium state. Due to this self-bias, the woven tubular member 110 may try to return to the equilibrium state when not in the equilibrium state (e.g., when in the initially-deployed state, etc.). The woven tubular member 110 may exert a force on the upper esophagus pouch 22 and the lower esophagus pouch 24, which may stretch and/or promote growth of the upper esophagus pouch 22 and the lower esophagus pouch 24 toward each other, as the woven tubular member 110 transitions toward the equilibrium state. The first flange 122 moves toward the second flange 132 as the woven tubular member 110 transitions from the initially-deployed state toward the equilibrium state.

Figure 11:
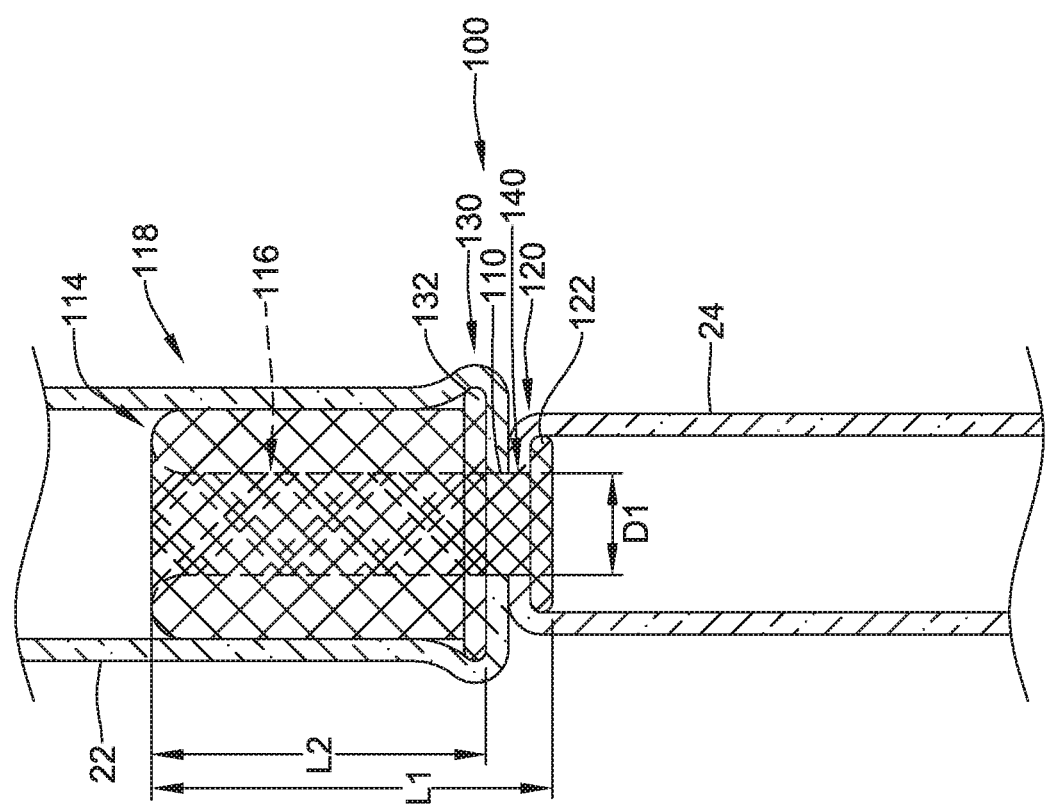

FIG. 11 illustrates a state of the woven tubular member 110 wherein the upper esophagus pouch 22 and the lower esophagus pouch 24 have been drawn together and/or have grown and are in abutting and/or mating contact with each other. In some embodiments, the state shown in FIG. 11 may be the equilibrium state of the woven tubular member 110. Alternatively, the woven tubular member 110 may continue to transition toward the equilibrium state as will be discussed below. In embodiments where FIG. 11 represents the equilibrium state and/or where treatment of esophageal atresia is considered complete from a growth perspective, the upper esophagus pouch 22 and the lower esophagus pouch 24 may be fixedly and permanently secured together. For example, the upper esophagus pouch 22 may be sutured and/or bonded (e.g., adhered) to the lower esophagus pouch 24 to form a completed esophagus forming a continuous, uninterrupted lumen between the mouth and the stomach of the patient. In some embodiments, the medical device 100 may be removed from the patient following fixed and permanent securement of the upper esophagus pouch 22 to the lower esophagus pouch 24. In some embodiments, the medical device 100 may be left in place as a permanent support structure for the esophagus.

As may be seen from FIG. 11, a portion of the body portion 140 is everted from the inner region 116 to the outer region 118 as the woven tubular member 110 transitions from the initially-deployed state toward the equilibrium state. The axial length L1 of the inner region 116 of the body portion 140 further decreases and the axial length L2 of the outer region 118 of the body portion 140 further increases as the woven tubular member 110 transitions from the initially-deployed state toward the equilibrium state (e.g., compared to FIG. 10). The outer diameter D1 of the inner region 116 of the body portion 140 further increases as the axial length L1 of the inner region 116 of the body portion 140 further decreases and/or as the woven tubular member 110 transitions from the initially-deployed state toward the equilibrium state (e.g., compared to FIG. 10).

In some embodiments, the medical device 100 and/or the woven tubular member 110 may continue to transition from the state shown in FIG. 11 to the equilibrium state shown in FIG. 12. In the equilibrium state of FIG. 12, a portion of the lower esophagus pouch 24 may be drawn and/or pulled through the opening in the upper esophagus pouch 22 such that the portion of the lower esophagus pouch 24 is disposed within and/or inside of the portion of the upper esophagus pouch 22 to create axial tissue overlap between the upper esophagus pouch 22 and the lower esophagus pouch 24. In the equilibrium state, the first flange 122 may be disposed within the outer region 118 of the body portion 140 of the woven tubular member 110. In some embodiments, the outer region 118 of the body portion 140 of the woven tubular member 110 surrounds the first flange 122 in the equilibrium state.

In some embodiments, the second flange 132 may be axially offset to a first axial side of the first flange 122 in the initially-deployed state (e.g., FIG. 9) and the second flange 132 may be axially offset to a second axial side of the first flange 122 in the equilibrium state (e.g., FIG. 12), wherein the second axial side of the first flange 122 is opposite the first axial side of the first flange 122 along the central longitudinal axis. For example, a transverse plane extending through the first flange 122 perpendicular to the central longitudinal axis may define the first axial side and the second axial side of the first flange 122. In the initially-deployed state, the second flange 132 may be disposed on the first axial side of the transverse plane, and in the equilibrium state, the second flange 132 may be disposed on the second axial side of the transverse plane.

The axial length L1 of the inner region 116 of the body portion 140 further decreases and the axial length L2 of the outer region 118 of the body portion 140 further increases as the woven tubular member 110 transitions from the initially-deployed state toward the equilibrium state (e.g., compared to FIG. 11). The outer diameter D1 of the inner region 116 of the body portion 140 further increases as the axial length L1 of the inner region 116 of the body portion 140 further decreases and/or as the woven tubular member 110 transitions from the initially-deployed state toward the equilibrium state (e.g., compared to FIG. 11). The outer diameter D1 of the inner region 116 of the body portion 140 may increase to a configuration wherein an outer surface of the lower esophagus pouch 24 is pressed into close proximity and/or into facing and/or abutting contact with an inner surface of the upper esophagus pouch 22, as seen in FIG. 12. The upper esophagus pouch 22 and the lower esophagus pouch 24 may be fixedly and permanently secured together. For example, the upper esophagus pouch 22 may be sutured and/or bonded (e.g., adhered) to the lower esophagus pouch 24 to form a completed esophagus forming a continuous, uninterrupted lumen between the mouth and the stomach of the patient. In some embodiments, proximity and/or contact between the upper esophagus pouch 22 and the lower esophagus pouch 24 may cause and/or result in the tissues growing together and/or bonding to each other naturally without the aid of outside assistance, structures, agents, and/or surgical intervention.

In some embodiments, axial tissue overlap between the upper esophagus pouch 22 and the lower esophagus pouch 24 may provide an improved seal between the upper esophagus pouch 22 and the lower esophagus pouch 24 via a larger landing zone of tissue therebetween. In some embodiments, the medical device 100 may be removed from the patient following fixed and permanent securement of the upper esophagus pouch 22 to the lower esophagus pouch 24. In some embodiments, the medical device 100 may be left in place as a permanent support structure for the esophagus.

As may be appreciated, in some embodiments, the medical device 100 may include the covering 150 disposed on the woven tubular member 110, as discussed herein, throughout the transition shown in FIGS. 9-12. The covering 150 may be configured to cooperate with the woven tubular member 110, the upper esophagus pouch 22, and the lower esophagus pouch 24 to permit and/or promote a "normal" nutritional intake into the patient by providing a temporary, artificial esophagus between the upper esophagus pouch 22 and the lower esophagus pouch 24. This may reduce the need for long-term sedation and/or immobilization of the patient during treatment.

The materials that can be used for the various components of the mandrel 50, the tubular spacer 60, the medical device 100, the woven tubular member 110, the covering 150, the delivery device 190, the system 200, etc. (and/or other systems or components disclosed herein) and the various elements thereof disclosed herein may include those commonly associated with medical devices. For simplicity purposes, the following discussion makes reference to the mandrel 50, the tubular spacer 60, the medical device 100, the woven tubular member 110, the covering 150, the delivery device 190, the system 200, etc. However, this is not intended to limit the devices and methods described herein, as the discussion may be applied to other elements, members, components, or devices disclosed herein, such as, but not limited to, the one or more filaments 112, etc. and/or elements or components thereof.

In some embodiments, the mandrel 50, the tubular spacer 60, the medical device 100, the woven tubular member 110, the covering 150, the delivery device 190, the system 200, etc., and/or components thereof may be made from a metal, metal alloy, a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-superelastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the mandrel 50, the tubular spacer 60, the medical device 100, the woven tubular member 110, the covering 150, the delivery device 190, the system 200, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the mandrel 50, the tubular spacer 60, the medical device 100, the woven tubular member 110, the covering 150, the delivery device 190, the system 200, etc. Some examples of radiopaque materials can include, but are not limited to, gold, platinum, palladium, tantalum, tungsten alloy, polymer material loaded with a radiopaque filler, and the like. Additionally, other radiopaque marker bands and/or or coils may also be incorporated into the design of the mandrel 50, the tubular spacer 60, the medical device 100, the woven tubular member 110, the covering 150, the delivery device 190, the system 200, etc. to achieve the same result.

In some embodiments, a degree of Magnetic Resonance Imaging (MM) compatibility is imparted into the mandrel 50, the tubular spacer 60, the medical device 100, the woven tubular member 110, the covering 150, the delivery device 190, the system 200, etc. For example, the mandrel 50, the tubular spacer 60, the medical device 100, the woven tubular member 110, the covering 150, the delivery device 190, the system 200, etc., and/or components or portions thereof, may be made of a material that does not substantially distort the image and create substantial artifacts (e.g., gaps in the image). Certain ferromagnetic materials, for example, may not be suitable because they may create artifacts in an Mill image. The mandrel 50, the tubular spacer 60, the medical device 100, the woven tubular member 110, the covering 150, the delivery device 190, the system 200, etc., or portions thereof, may also be made from a material that the Mill machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the mandrel 50, the tubular spacer 60, the medical device 100, the woven tubular member 110, the covering 150, the delivery device 190, the system 200, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the medical device 100, the woven tubular member 110, the covering 150, the delivery device 190, the system 200, etc. disclosed herein may include a fabric material disposed over or within at least a portion of the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device 100, the woven tubular member 110, the covering 150, the delivery device 190, the system 200, etc. may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device 100, the woven tubular member 110, the covering 150, the delivery device 190, the system 200, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device for treating esophageal atresia, comprising:
    a woven tubular member having a first end, a second end, and a body portion extending between the first end and the second end;
    the first end having a first flange extending radially outwardly from the body portion;
    the second end having a second flange extending radially outwardly from the body portion;
    wherein the woven tubular member is configured to transition from an initially-deployed state toward an equilibrium state;
    wherein in the initially-deployed state, the body portion includes an inner region extending from the first flange to a transition region and an outer region extending from the second flange to the transition region;
    wherein the outer region surrounds the inner region;
    wherein the woven tubular member is self-biased to be in the equilibrium state;
    wherein an axial length of the inner region decreases and an axial length of the outer region increases as the woven tubular member transitions from the initially-deployed state toward the equilibrium state.

2. The medical device of claim 1, wherein in the equilibrium state, the first flange is disposed within the outer region.

3. The medical device of claim 1, further comprising a covering disposed on at least a portion of the woven tubular member.

4. The medical device of claim 3, wherein at least one of the first flange and the second flange includes the covering.

5. The medical device of claim 3, wherein the covering at least partially encapsulates the woven tubular member.

6. The medical device of claim 1, wherein an outer diameter of the inner region increases as its axial length decreases.

7. The medical device of claim 1, wherein a portion of the body portion is everted from the inner region to the outer region as the woven tubular member transitions from the initially-deployed state toward the equilibrium state.

8. A medical device for treating esophageal atresia, comprising:
    a woven tubular member having a first end, a second end, and a body portion extending between the first end and the second end;
    the first end having a first flange extending radially outwardly from the body portion;

the second end having a second flange extending radially outwardly from the body portion; and the body portion having an inner region extending from the first flange to a transition region and an outer region extending from the second flange to the transition region;

wherein the outer region surrounds the inner region;

wherein the woven tubular member is configured to transition from an initially-deployed state toward an equilibrium state;

wherein in the initially-deployed state, the woven tubular member has a proximalmost extent and a distalmost extent, the second flange being positioned at a location intermediate the proximalmost extent and the distalmost extent;

wherein a portion of the body portion is everted from the inner region to the outer region as the woven tubular member transitions from the initially-deployed state toward the equilibrium state.

9. The medical device of claim 8, wherein the first flange moves toward the second flange as the woven tubular member transitions from the initially-deployed state toward the equilibrium state.

10. The medical device of claim 9, wherein the outer region of the woven tubular member surrounds the first flange in the equilibrium state.

11. The medical device of claim 10, wherein an outer diameter of the inner region increases as the woven tubular member transitions from the initially-deployed state toward the equilibrium state.

12. A medical device for treating esophageal atresia, comprising:

a woven tubular member having a first end, a second end, and a body portion extending between the first end and the second end;

the first end having a first flange extending radially outwardly from the body portion;

the second end having a second flange extending radially outwardly from the body portion;

wherein the woven tubular member is configured to transition from an initially-deployed state toward an equilibrium state;

wherein in the initially-deployed state, the body portion includes an inner region extending from the first flange to a transition region and an outer region extending from the second flange to the transition region;

wherein the outer region surrounds the inner region;

wherein the woven tubular member is self-biased to be in the equilibrium state;

wherein a portion of the body portion is everted from the inner region to the outer region as the woven tubular member transitions from the initially-deployed state toward the equilibrium state.

13. The medical device of claim 12, wherein in the equilibrium state, the first flange is disposed within the outer region.

14. The medical device of claim 12, further comprising a covering disposed on at least a portion of the woven tubular member.

15. The medical device of claim 14, wherein at least one of the first flange and the second flange includes the covering.

16. The medical device of claim 14, wherein the covering at least partially encapsulates the woven tubular member.

17. The medical device of claim 12, wherein an outer diameter of the inner region increases as its axial length decreases.

18. The medical device of claim 12, wherein the first flange moves toward the second flange as the woven tubular member transitions from the initially-deployed state toward the equilibrium state.

19. The medical device of claim 18, wherein the outer region of the woven tubular member surrounds the first flange in the equilibrium state.

* * * * *